United States Patent [19]

Lew et al.

[11] Patent Number: 4,694,179
[45] Date of Patent: Sep. 15, 1987

[54] SYMBIOTIC FILTER-STERILIZER

[76] Inventors: Hyok S. Lew, 7890 Oak St., Arvada, Colo. 80005; Michael Stranahan, 2858 Woody Creek Rd., Woody Creek, Colo. 81656

[21] Appl. No.: 866,893

[22] Filed: May 27, 1986

[51] Int. Cl.$^4$ ........................................... G01N 21/01
[52] U.S. Cl. ................... 250/431; 250/436; 250/438; 422/24; 422/186.3; 210/760
[58] Field of Search ............... 250/436, 437, 438, 431; 422/24; 261/DIG. 42; 210/760; 422/186.1, 186.3

[56] References Cited

U.S. PATENT DOCUMENTS

| | | | |
|---|---|---|---|
| 2,738,427 | 3/1956 | Wagon | 250/431 |
| 3,923,663 | 12/1975 | Reid | 422/24 |
| 4,033,719 | 7/1977 | Conn et al. | 250/438 |
| 4,087,925 | 5/1978 | Bienek | 250/437 |
| 4,141,830 | 2/1979 | Last | 422/24 |

OTHER PUBLICATIONS

"U.V./Ozone Cleaning of Surface", Vig et al., IEEE Transaction on Parts, Hybrids, and Packaging, vol. PHP-12, No. 4, Dec. 1976, pp. 365-370, 250-431.

Primary Examiner—Bruce C. Anderson

[57] ABSTRACT

This invention relates to a device including a combination of a porous filter and ultraviolet light source, that is for purifying fluid media. The porous filter filtering out particles suspended in the fluid medium and the ultraviolet germicidal lamp killing germs in the fluid medium are arranged in a combination in such a way that the porous filter distributes the fluid flow in a pattern that exposes the fluid medium to the germicidal radiation uniformly and thoroughly, while the ultraviolet germidical light destroys the bacteria and other germs contaminating the fluid medium, and at the same time cleans the porous filter continuously by oxidizing the organic particles clogging the porous filter wherein the oxidizing process utilizes oxygen naturally dissolved in the fluid medium or that artificially injected into the fluid medium.

4 Claims, 5 Drawing Figures

SYMBIOTIC FILTER-STERILIZER

SUMMARY OF THE INVENTION

As our environment becomes more and more contaminated by the ever increasing human population and industrial production demanded thereby, there arises an ever increasing requirement for filtering and sterlizing the air and water that we breath and drink and other fluid mediums used in our daily living and industrial activities. One of the most serious and frequent problems occuring in filtering operations in industrial plants as well as domestic applications is the clogging of the pores of the porous filters. In the present day practice, the clogged filter is cleaned by immersing the filter in an acid or base solution or by forcing an acid or base solution through the filter. In general, the clogged filter has to be removed from the installation for cleaning. If the clogged filter is cleaned in line, it has to be rinsed thoroughly before starting up the filtering operation again. Whether the clogged filter is cleaned in place or after removal, the filtering operation has to be interrupted in the present day practice. Further more, the present day practice of cleaning clogged filters produces toxic waste solutions which have to be treated before dumping them into the environment. It is quite clear that, in many cases, the present day practice of cleaning clogged filters is less than satisfactory from the operational point of view as well as the environmental point of view. Therefore, there exists a strong demand for a few new method of cleaning clogged filters.

The primary object of the present invention is to provide a filter-sterilizer combination functioning in a symbiotic relationship, wherein the porous filter not only filters out the particles entrained in the fluid medium but also distributes the fluid flow favorably for uniform and through sterilization by the germicidal light, while the germicidal light not only sterilizes the fluid medium by the irradiation of the ultraviolet radiation but also continuously cleans the filter by oxydizing the organic matters clogging the pores of the filter.

Another object is to provide a method for continuously cleaning the filters without removing the filters and without interrupting the filtering operation.

A further object is to provide a method for cleaning the filters without producing any toxic waste solutions.

Still another object is to provide a filter-sterilizer combination that is safe and economic for industrial as well as domesitic use.

Still a further object is to provide a filter-sterilizer combination that operates for years without requiring any servicing or maintenance as the operation and use thereof cleans and rejuvenates the filter continuously.

These and other objects of the present invention will become clear as the description thereof proceeds.

BRIEF DESCRIPTION OF FIGURES

The present invention may be described with greater clarity and specificity by referring to the following figures.

DESCRIPTION OF THE ILLUSTRATED EMBODIMENTS

Figure 1:
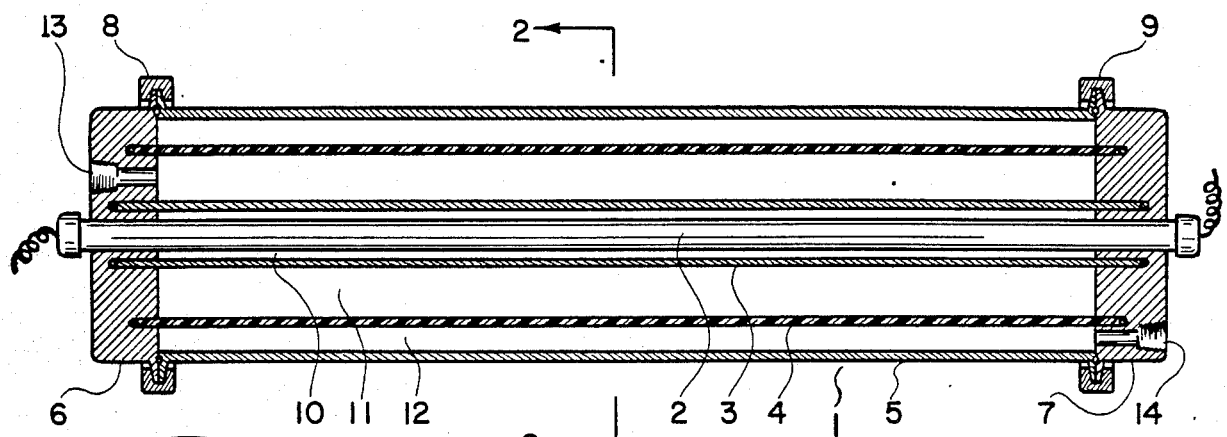
FIG. 1 illustrates a cross section view of the symbiotic filter-sterilizer combination arranged in accordance with the principles of the present invention.

In FIG. 1 there is illustrated a cross section of the symbiotic filter-sterilizer combination arranged in accordance with the principles of the present invention, which cross section is taken along a plane including the central axis of the symbiotic filter-sterilizer 1 having a cylindrical assembly. The elongated ultraviolet light source 2 is substantially coaxially disposed within an ultraviolet light transparent tubing 3. The combination of the elongated ultraviolet light source 2 and the transparent tube 3 is substantially coaxially disposed within a cylindrical shell filter 4 having a porous wall, which is then disposed within a cylindrical shell 5 having a solid wall. The two extremities of the assembly including the elongated germicidal lamp, the ultraviolet transparent tubing 3, the cylindrical tubular filter 4 and the cylindrical shell container 5 are secured in place by the two end members 6 and 7, which are connected to the extremities of the cylindrical shell container 5 a pair of clamp adapters 8 and 9, respectively. The two end members 6 and 7 retain the elongated ultraviolet lamp 2, the ultraviolet transparent tubing 3, and the cylindrical tubular filter 4 at appropriate positions within the sealed containing member comprising the cylindrical shell 5 and two end members 6 and 7 assembled in a leak proof manner. As the extremities of each element disposed within the cylindrical shell 5 engage appropriate grooves with seals included in the end members 6 and 7, those members are securely held at proper positions and provide leak-proof barriers, which divide the space inside the leak-proof container comprising the cylindrical shell 5 and two end members 6 and 7 into a series of annular compartments 10, 11 and 12. The end member 6 includes a port 13 open to the annular compartment 11, providing a flow passage into or out of that compartment. A port 14 disposed through the end member 7 and open to the annular compartment 12 provides a flow passage into or out of the annular compartment 12.

Figure 2:
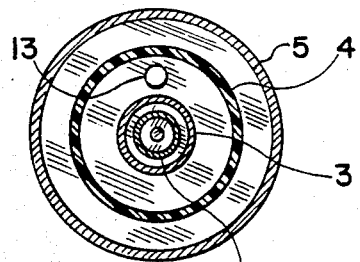
FIG. 2 illustrates another cross section of the filter-sterilizer combination illustrated in FIG. 1 taken along plane 2—2 as shown in FIG. 1.

In FIG. 2 there is illustrated another cross section of the symbiotic filter-sterilizer illustrated in FIG. 1, which cross section is taken along plane 2—2 as shown in FIG. 1. The substantially coaxial arrangements including the elongated ultraviolet lamp 2, the ultraviolet transparent tubing 3, the tubular filter 4 and the cylindrical shell 5 is clearly shown in this figure.

The symbiotic filter-sterilizer illustrated in FIGS. 1 and 2 operates in the following principles: The fluid medium to be filtered and sterlized either enters through the port 14 and leaves through the port 13 or enters through the port 13 and leaves through the port 14. The fluid medium is filtered as it flows across the tubular filter 4 with a porous wall and is sterilized by the ultraviolet light as the fluid medium flows by the elongated ultraviolet light source 2. The ultraviolet light irradiating on and penetrating porous wall of the cylindrical tubular filter 4 oxidizes the organic particles clogging the pores of the tubular filter 4, which oxidizing action results from the ultraviolet light converting the dissolved oxygen in the medium to ozone which is a powerful oxidizing agent. As a consequence, the tubular filter 4 is cleaned continuously while it is in use wherein the organic particles clogging the pores of the filter are oxidized and converted into harmless gases. The particles clogging the pores of the filter which are not oxidized by the ozone can be gotten rid of by back-flushing the filter. Of course, the tubular filter 4 has to be made of material inert to ultraviolet light such as the ceramics, flourocarbon based material, etc. The ultraviolet transparent tubular window 3 must be made of hard glass that does not solarize in time. The germicidal action of the ultraviolet light is carried out either by direct irradiation on the bacteria or by the production of ozone killing bacteria by oxidation. The tubular filter 4 enhances the germicidal action of the ultraviolet light, as the slowly moving fluid medium flowing across the filter in a substantially uniform distribution is exposed uniformly and thoroughly to the ultraviolet light and the oxidizing effect thereof. In conclusion, the ultraviolet light source 2 and the tubular filter 3 play the symbiotic role, as the former keeps the latter from clogging while the latter enhances the germicidal action by the former. For this reason, the device taught by the present invention is called the "symbiotic filter-sterilizer".

Figure 3:
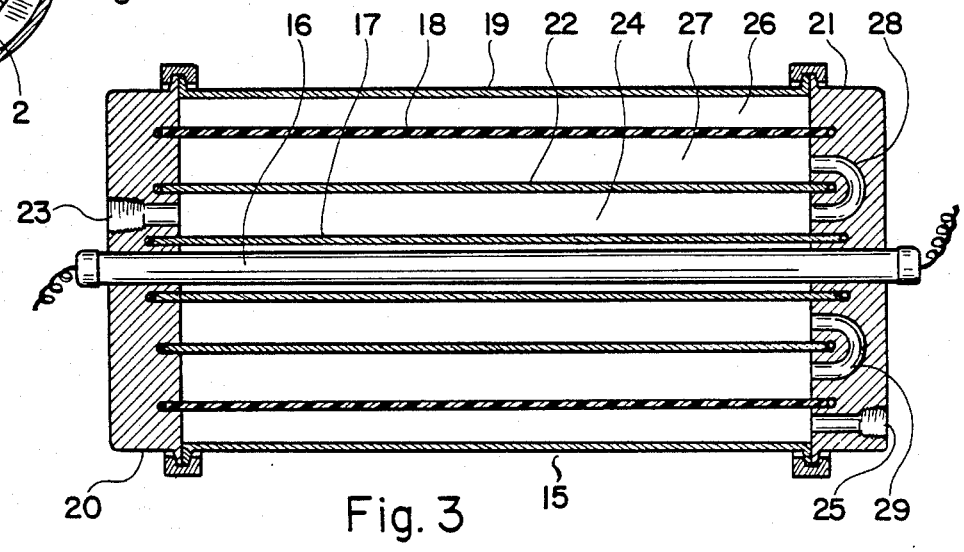
FIG. 3 illustrates another embodiment of the symbiotic filter-sterilizer combination arranged in accordance with the principles of the present invention.

In FIG. 3 there is illustrated a cross section of another embodiment of the filter-sterilizer constructed in accordance with the principles of the present invention, which cross section is taken along a plane including the central axis of the device. The symbiotic filter-sterilizer 15 includes essentially the same elements arranged in essentially the same way as the embodiment illustrated in FIG. 1, that includes the ultraviolet lamp 16, the transparent tubular shield 17, the cylindrical shell filter 18 with porous wall, the outer cylindrical shell 19 arranged in a coaxial arrangement, and a pair of end members 20 and 21. In addition to the aforementioned elements, the symbiotic filter-sterilizer illustrated in FIG. 3 further includes a cylindrical shell partition 22 transmitting ultraviolet rays disposed intermediate the transparent tubular shield 17 and the cylindrical shell filter 18 in a substantially coaxial relationship. These elements are arranged in a leak proof manner wherein each annular compartment is isolated from the other. A first port 23 open to the annular compartment 24 intermediate the transparent tubular shield 17 and the cylindrical shell partition 22 is disposed through the first end member 20, while a second port 25 open to the annular compartment 26 intermediate the cylindrical shell filter 18 and the outer cylindrical shell 19 is disposed through the second end member 21. The annular compartment 24 in the interior of the cylindrical shell partition 22 is open to the annular compartment 27 intermediate the cylindrical shell partition 22 and the cylindrical shell filter 18 by a plurality of flow passages 28, 29, etc. In the embodiment of the symbiotic filter-sterilizer illustrated in FIG. 3, the fluid makes a complete pass from one end to the other end of the apparatus fully exposed to the germicidal light either before or after flowing across the cylindrical shell filter 18. As a consequence, the fluid is more thoroughly sterilized.

Figure 4:
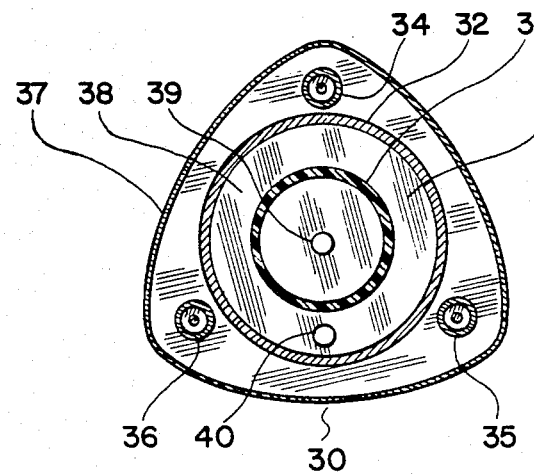
FIG. 4 illustrates a further embodiment of the symbiotic filter-sterilizer combination of the present invention.

In FIG. 4, there is illustrated a cross section of a further embodiment 30 of the symbiotic filter-sterilizer of the present invention, which cross section is taken along a plane perpendicular to the cylindrical axis of the arrangement. The cylindrical shell filter 31 is coaxially disposed within the transparent outer cylindrical shell 32 wherein the two members 31 and 32 are secured between the two end members including one end member 33 shown in this cross section view and the other member that is not shown. A plurality of the elongated germicidal lamps 34, 35, 36, etc. are disposed in a substantially axisymmetric pattern external to the transparent outer cylindrical shell and internal to the ultraviolet light reflector shell 37. The reflector shell 37 is shaped in such a way that the entire annular compartment 38 intermediate the transparent outer shell 32 and the cylindrical shell filter 31 is uniformly irradiated by the germicidal light emitting directly from the germicidal lamps or reflected by the reflector shell 37. The first port 39 is open to the compartment interior to the cylindrical shell filter 31, while the second port 40 is open to the annular compartment intermediate the cylindrical shell filter 31 and the transparent outer shell 32. This embodiment of the symbiotic filter-sterilizer operates by the same principles as that described in conjunction with FIG. 1.

Figure 5:
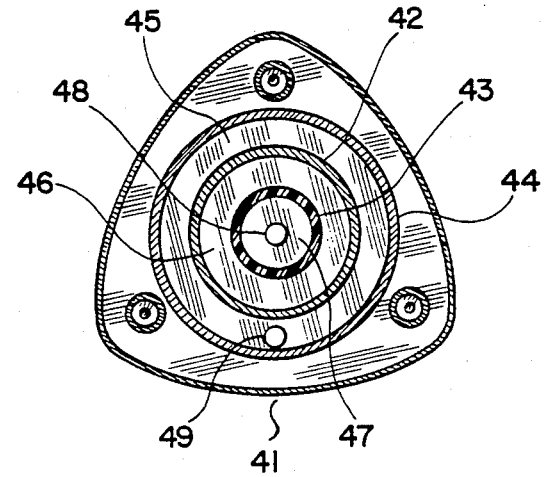
FIG. 5 illustrates still another embodiment of the symbiotic filter-sterilizer combination of the present invention.

In FIG. 5, there is illustrated a cross section of yet another embodiment of the symbiotic filter-sterilizer of the present invention, which cross section is taken along a plane perpendicular to the cylindrical axis of the apparatus. The symbiotic filter-sterilizer 41 includes the same elements arranged in the same construction as the apparatus shown in FIG. 4. Additionally it includes the cylindrical shell partition 42 transmitting ultraviolet rays disposed intermediate the cylindrical shell filter 43 and the transparent outer shell 44. The annular compartment 45 external to the cylindrical shell partition 42 and the annular compartment 46 internal of the cylindrical shell partition 42 is open to one another by means of a plurality of flow passages similar to those elements 28, 29, etc. shown in FIG. 3, which flow passages are included in the end member opposite to the end member 47, that is not shown in FIG. 5. The first port 48 is open to the compartment interior to the cylindrical shell filter 43, while the second port 49 is open to the annular compartment intermediate the cylindrical shell partition 42 and the transparent outer cylindrical shell 44. The embodiment provides an improved germicidal capability in the same way as that described in conjunction with FIG. 3. It is evident that one or more germicidal lamps protected by a transparent shield may be disposed within the cylindrical shell filter in addition to the germicidal lamps shown in FIGS. 4 and 5, as taught by the embodiments illustrated in FIGS. 1 and 3.

While the principles of the present invention have now been made clear by the illustrative embodiments it will be immediately obvious to the skilled in the art that many modifications of the structures, arrangement, proportions, elements and materials, can be made which are particularly adapted to the specific working environments and operating conditions in the practice of the invention without departing from those principles of the present invention.

We claim:

1. A symbiotic filter-sterilizer for filtering and sterilizing a fluid, comprising in combination:
  (a) a cylindrical shell having a first and a second closed ends;
  (b) a tubular filter having a porous cylindrical wall disposed within said cylindrical shell wherein said tubular filter extending from said one closed end to said the other closed end provides a first annular compartment intermediate said cylindrical shell and said tubular filter;

(c) a transparent tubular shield transmitting ultraviolet rays disposed within said tubular filter, wherein said transparent tubular shield extending from said one closed end to said the other closed end provides a second annular compartment intermediate said tubular filter and said transparent tubular shield;

(d) at least one elongated germicidal lamp for emiting ultraviolet rays disposed within said transparent tubular shield;

(e) at least one port open to said first annular compartment providing a flow passage for fluid; and (f) at least one port open to said second annular compartment providing a flow passage for fluid;

wherein the ultraviolet rays emitted by said germicidal lamp sterilizes the fluid being circulated through said first and second annular compartments and filtered by said tubular filter, and cleans said tubular filter by oxidizing particles clogging up the pores of said tubular filter, while said tubular filter enhances the sterilizing effect of said germicidal lamp by distributing the fluid flow for uniform exposure to the ultraviolet rays.

2. The combination as set forth in claim 1 wherein said combination includes a cylindrical shell partition transmitting ultraviolet rays disposed within said second annular compartment in a substantially coaxial relationship, wherein said cylindrical shell partition extending from said one closed end to said the other closed end partitions said second annular compartment into a third annular compartment exterior to said cylindrical shell partition and a fourth annular compartment interior to said cylindrical shell partition wherein said at least one port open to said second annular compartment is now open to said fourth annular compartment, said combination further including at least one flow passage connecting said third and fourth annular compartments to one another.

3. A symbiotic filter-sterilizer for filtering and sterilizing a fluid, comprising in combination:

(a) a transparent cylindrical shell transmitting ultraviolet rays, said transparent cylindrical shell having a first and a second closed ends;

(b) a tubular filter having a porous cylindrical wall disposed within said transparent cylindrical shell, wherein said tubular filter extending from said one closed end to said the other closed end provides a first annular compartment intermediate said transparent cylindrical shell and said tubular filter;

(c) at least one elongated germicidal lamp for emitting ultraviolet rays disposed exterior to said transparent cylindrical shell in a substantially parallel configuration with respect to said transparent cylindrical shell;

(d) an ultraviolet ray reflecting surface substantially surrounding the combination of said elongated germicidal lamp and said transparent cylindrical shell for directing the ultraviolet rays towards said first annular compartment;

(e) at least one port open to said first annular compartment; and (f) at least one port open to a cylindrical compartment interior to said tubular filter;

wherein the ultraviolet rays emitted by said germicidal lamp sterilizes the fluid being circulated through said first annular compartment and said cylindrical compartment and filtered by said tubular filter, and cleans said tubular filter by oxdizing particles clogging up the pores of said tubular filter, while said tubular filter enhances the steriziling effect of said germicidal lamp by distributing the fluid flow for uniform exposure to the ultraviolet rays.

4. The combination as set forth in claim 3 wherein said combination includes a cylindrical shell partition transmitting ultraviolet rays disposed within said first annular compartment in a substantially coaxial relationship, wherein said cylindrical shell partition extending from said one closed end to said the other closed end partitions said first annular compartment into a second annular compartment exterior to said cylindrical shell partition and a third annular compartment interior to said cylindrical shell partition wherein said at least one port open to said first annular compartment is now open to said second annular compartment, said combination further including at least one flow passage connecting said second and third annular compartments to one another.

* * * * *